(12) United States Patent
Zhu

(10) Patent No.: US 11,529,098 B2
(45) Date of Patent: Dec. 20, 2022

(54) CONTACT LENS, SYSTEM AND METHOD FOR MONITORING GLUCOSE

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Lin Zhu, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 399 days.

(21) Appl. No.: 16/904,755

(22) Filed: Jun. 18, 2020

(65) Prior Publication Data

US 2020/0315535 A1    Oct. 8, 2020

Related U.S. Application Data

(63) Continuation-in-part of application No. PCT/CN2019/110383, filed on Oct. 10, 2019.

(30) Foreign Application Priority Data

Oct. 11, 2018    (CN) .......................... 201811185859.9

(51) Int. Cl.
*A61B 5/00* (2006.01)
*G06T 7/90* (2017.01)
(Continued)

(52) U.S. Cl.
CPC ............ *A61B 5/6821* (2013.01); *A61B 3/101* (2013.01); *A61B 5/1455* (2013.01);
(Continued)

(58) Field of Classification Search
CPC ... A61B 5/6821; A61B 3/101; A61B 5/14507; A61B 5/14532; A61B 5/1455;
(Continued)

(56) References Cited

U.S. PATENT DOCUMENTS

2017/0162072 A1\* 6/2017 Horseman ............ A61B 5/6803
2018/0267331 A1\* 9/2018 Abbasi ............ B29D 11/00807
2020/0315535 A1   10/2020 Zhu

FOREIGN PATENT DOCUMENTS

| CN | 1734314 A | 2/2006 |
| CN | 101793996 A | 8/2010 |
| CN | 102350315 A | 2/2012 |
| CN | 105974611 A | 9/2016 |

(Continued)

OTHER PUBLICATIONS

First Office Action issued in Chinese Patent Application No. 201811185859.9, dated Nov. 1, 2019; with English translation.
(Continued)

*Primary Examiner* — Roy M Punnoose
(74) *Attorney, Agent, or Firm* — McDermott Will & Emery LLP

(57) ABSTRACT

A contact lens includes a contact lens body and a glucose detection sheet disposed on the contact lens body. The glucose detection sheet includes a glucose recognition layer, a photonic crystal array is provided in the glucose recognition layer, and the glucose recognition layer is configured to recognize glucose.

20 Claims, 11 Drawing Sheets

(51) Int. Cl.
*A61B 3/10* (2006.01)
*A61B 5/145* (2006.01)
*A61B 5/1455* (2006.01)
*G01N 21/31* (2006.01)
*G06T 7/00* (2017.01)
*G08B 21/02* (2006.01)

(52) U.S. Cl.
CPC ...... *A61B 5/14507* (2013.01); *A61B 5/14532* (2013.01); *G01N 21/31* (2013.01); *G06T 7/0012* (2013.01); *G06T 7/90* (2017.01); *A61B 2562/0233* (2013.01); *A61B 2562/046* (2013.01); *G06T 2207/30041* (2013.01); *G08B 21/02* (2013.01)

(58) Field of Classification Search
CPC ...... A61B 2562/0233; A61B 2562/046; A61B 3/10; G01N 21/31; G01N 21/7743; G01N 21/78; G01N 21/01; G06T 7/0012; G06T 7/90; G06T 2207/30041; G06T 2207/10024; G08B 21/02
See application file for complete search history.

(56) References Cited

FOREIGN PATENT DOCUMENTS

| | | |
|---|---|---|
| CN | 106037756 A | 10/2016 |
| CN | 107056981 A | 8/2017 |
| CN | 107556509 A | 1/2018 |
| CN | 109297913 A | 2/2019 |

OTHER PUBLICATIONS

Second Office Action issued in Chinese Patent Application No. 201811185859 9, dated Apr. 20, 2020; with English translation.
Third Office Action issued in Chinese Patent Application No. 201811185859 9, dated Aug. 27, 2020; with English translation.
Decision of Rejection issued in Chinese Patent Application No. 201811185859.9, dated Dec. 3, 2020; with English translation.
Xue, Fei, "Molecularly Imprinted Photonic Crystal for Detection of Glucose," Chinese Journal of Analytical Chemistry, Jul. 2011, 39(7); pp. 1015-1020; with English translation.
International Search Report and Written Opinion issued in International Patent Application No. PCT/CN2019/110383, dated Dec. 30, 2019; with English translation.

* cited by examiner

CONTACT LENS, SYSTEM AND METHOD FOR MONITORING GLUCOSE

CROSS-REFERENCE TO RELATED APPLICATIONS

This application is a Bypass Continuation-in-Part Application of PCT/CN2019/110383 filed on Oct. 10, 2019, which claims priority to Chinese Patent Application No. 201811185859.9 filed on Oct. 11, 2018, which are incorporated herein by reference in their entirety.

TECHNICAL FIELD

The present disclosure relates to the field of glucose detection technologies, and in particular, to a contact lens, and a system and a method for monitoring glucose.

BACKGROUND

The glucose concentration in the human body is also called blood sugar level. The normal glucose concentration in the blood of a person ranges from 4.4 mmol/L to 6.6 mmol/L (80 mg/dL to 120 mg/dL). When the glucose concentration in the blood is too low, the brain tissues cannot get enough energy, and their functions will be inhibited or impaired. When the glucose concentration in the blood is too high, if the insulin is not sufficient, the glucose cannot be fully utilized and will remain in the blood, causing "high blood sugar". Long-term "high blood sugar" will seriously damage various internal organs and external organs of the human body, leading to diseases such as kidney failure or blindness.

SUMMARY

In one aspect, a contact lens is provided. The contact lens includes a contact lens body and a glucose detection sheet disposed on the contact lens body. The glucose detection sheet includes a glucose recognition layer including a photonic crystal array provided therein, and the glucose recognition layer being configured to recognize glucose.

In some embodiments, the glucose recognition layer is a molecularly imprinted photonic crystal layer.

In some embodiments, the glucose detection sheet further includes: a first substrate disposed on a surface of the molecularly imprinted photonic crystal layer facing away from the contact lens body, the first substrate having first pore structures.

In some embodiments, the first substrate includes a paper-based substrate or a polymethyl methacrylate substrate.

In some embodiments, the glucose detection sheet further includes: a second substrate disposed between and in contact with the molecularly imprinted photonic crystal layer and the contact lens body, the second substrate having second pore structures.

In some embodiments, a material of the first substrate and a material of the second substrate are the same.

In some embodiments, a material of the contact lens body and a material of the second substrate are the same, and the contact lens body and the substrate are integrally formed.

In some embodiments, the contact lens body includes an eyeball contact surface and a first surface opposite to the eyeball contact surface; and the glucose detection sheet is disposed on the eyeball contact surface of the contact lens body or the first surface of the contact lens body.

In some embodiments, the contact lens body includes a corneal region and an eye white region around the corneal region, and the glucose detection sheet is disposed on the eye white region of the contact lens body.

In some embodiments, a shape of the glucose detection sheet is a rectangle, a circle, or a ring.

In some embodiments, the contact lens body includes a corneal region and an eye white region around the corneal region, and the corneal region includes a pupil region; and the shape of the glucose detection sheet is a ring, and the glucose detection sheet surrounds the pupil region of the contact lens body.

In another aspect, a system for monitoring glucose is provided. The system includes the contact lens according to any one of the foregoing embodiments; a spectrum sensing device configured to send a signal carrying spectral information of the glucose detection sheet in the contact lens to a processor after the glucose detection sheet senses a glucose concentration in tears of a user; and the processor coupled to the spectrum sensing device and configured to obtain a spectral redshift value of the glucose detection sheet according to the signal, so as to determine the glucose concentration in the tears of the user.

In some embodiments, the spectrum sensing device includes an image capture device configured to: capture an image of the contact lens after the glucose detection sheet senses the glucose concentration in the tears of the user, and send the image of the contact lens to the processor; and the processor is configured to obtain a spectral redshift value of the glucose detection sheet according to the image of the contact lens.

In some embodiments, the system further includes an early warning device coupled to the processor. The processor is further configured to: determine whether the glucose concentration in the tears of the user is within a preset threshold range, and send a warning control signal to the early warning device in response to a determination that the glucose concentration in the tears of the user is not within the preset threshold range. The early warning device is configured to send out a warning signal in response to receiving the warning control signal.

In some embodiments, the spectrum sensing device includes a light sensor. The light sensor is disposed on the glucose detection sheet, and a sensing surface of the light sensor faces the glucose detection sheet. The light sensor is configured to: sense light with wavelengths in a range of a spectrum of the glucose detection sheet after the glucose detection sheet senses the glucose concentration in the tears of the user, generate a sensing signal carrying spectral information, and send the sensing signal to the processor. The processor is configured to obtain the spectral redshift value of the glucose detection sheet according to the sensing signal.

In some embodiments, the system further includes a glucose regulating device coupled to the processor. The processor is further configured to determine whether the spectral redshift value of the glucose detection sheet exceeds a redshift threshold, and send a regulating control signal to the glucose regulating device in response to a determination that the spectral redshift value exceeds the redshift threshold. The glucose regulating device is configured to release a substance for reducing glucose concentration in response to receiving the regulating control signal.

In some embodiments, the glucose regulating device includes an insulin releasing device capable of being implanted under skin of the user.

In yet another aspect, a method for monitoring glucose is provided. The method is performed by the system for monitoring glucose according to some of the foregoing embodiments. The method includes: sensing, by the glucose detection sheet in the contact lens, the glucose concentration in the tears of the user; sending, by the spectrum sensing device, the signal carrying the spectral information of the glucose detection sheet to the processor after the glucose detection sheet senses the glucose concentration in the tears of the user; obtaining, by the processor, the spectral redshift value of the glucose detection sheet according to the signal, so as to determine the glucose concentration in the tears of the user.

In some embodiments, the system for monitoring glucose further includes an early warning device, and the method further includes: determining, by the processor, whether the glucose concentration in the tears of the user is within a preset threshold range; sending, by the processor, the warning control signal to the early warning device in response to a determination that the glucose concentration in the tears of the user is not within the preset threshold range; and sending out, by the early warning device, an warning signal in response to the warning control signal.

In some embodiments, the system for monitoring glucose further includes a glucose regulating device, and the method further includes: determining, by the processor, whether the spectral redshift value of the glucose detection sheet exceeds a redshift threshold; sending, by the processor, a regulating control signal to the glucose regulating device in response to a determination that the spectral redshift value of the glucose detection sheet exceeds the redshift threshold; and releasing, by the glucose regulating device, a substance for reducing glucose concentration in response to the regulating control signal.

BRIEF DESCRIPTION OF THE DRAWINGS

The accompanying drawings are used to provide further understanding of the present disclosure and constitute a part of embodiments of the present disclosure. The exemplary embodiments in the present disclosure and the descriptions thereof serve to explain the present disclosure, but do not constitute a limitation to the present disclosure. In the accompanying drawings.

DETAILED DESCRIPTION

Figure 1:
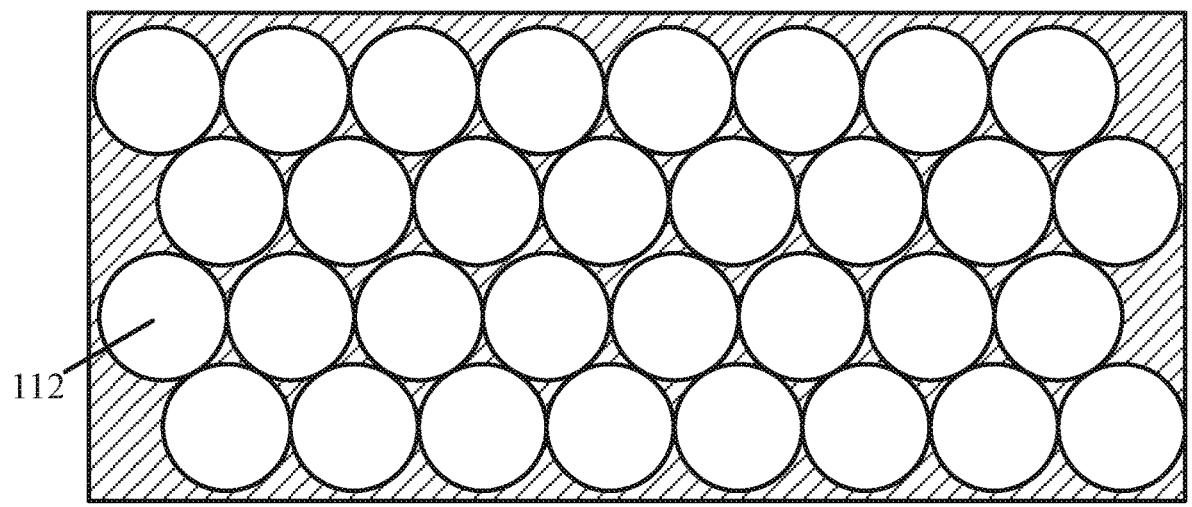
FIG. 1 is a schematic diagram showing a structure of a glucose detection sheet, in accordance with some embodiments.

The technical solutions in some embodiments of the present disclosure will be described clearly and completely with reference to the accompanying drawings. However, the described embodiments are merely some but not all of embodiments of the present disclosure. All other embodiments made on the basis of the embodiments of the present disclosure by a person of ordinary skill in the art shall be included in the protection scope of the present disclosure.

Any person skilled in the art may understand that, unless otherwise defined, all the terms used herein (including technical terms and scientific terms) have the same meanings as the general understanding of a person of ordinary skill in the art which the present disclosure belongs to. It should also be understood that terms such as those defined in an ordinary dictionary should be interpreted as have meanings consistent with their meanings in the context of the related art, and should not interpreted in an idealized or extremely formalized way unless explicitly defined herein.

Unless the context requires otherwise, the term "comprise/include" and other forms thereof such as the third-person singular form "comprises/includes" and the present participle form "comprising/including" in the description and the claims are construed as open and inclusive, i.e., "inclusive, but not limited to". In the description, the terms such as "one embodiment", "some embodiments", "exemplary embodiments", "example", "some examples", or "specific example" are intended to indicate that specific features, structures, materials or characteristics related to the embodiment(s) or the example(s) are included in at least one embodiment or example of the present disclosure. Schematic representations of the above terms do not necessarily refer to the same embodiment(s) or example(s). In addition, the specific features, structures, materials or characteristics may be included in any one or more embodiments/examples in any suitable manner.

The terms "first" and "second" are merely used for describing purpose, but cannot be construed as indicating or implying relative importance or implicitly indicating the number of the indicated technical features below. Thus, features defined by "first" and "second" may explicitly or implicitly include one or more of the features.

The terms such as "coupled", "connected" and their extensions are used in describing some embodiments. For example, the term "connected" may be used in description of some embodiments to indicate that two or more components are in direct physical or electrical contact with each other. For another example, the term "coupled" may be used in describing some embodiments to indicate that two or more components are in direct physical or electrical contact. However, the term "coupled" may also mean that two or more components are not in direct contact with each other, but still cooperate or interact with each other. For example, two or more components realize signal interaction, data transmission and reception through wireless connection manners such as WiFi (wireless network), Bluetooth, and general packet radio service (GPRS). The embodiments disclosed herein are not necessarily limited to the content in this description.

Glucose concentration in a human body is an important indicator to tell if a person is healthy. A glucose concentration that is too high or too low will cause health problems. The glucose concentration in the human body is represented by glucose concentration in the blood. In order to effectively detect the glucose concentration in the human blood, the practice of drawing blood is generally adopted. Although this method can produce accurate detection results of the glucose concentration in the blood, the detection efficiency is low, the cost is high, and the human body will be subject to some trauma.

As shown in FIGS. 4A to 5B, some embodiments of the present disclosure provide a contact lens 2. In addition to a function of helping a wearer to see things, the contact lens may detect the glucose concentration in the wearer's body. As shown in FIGS. 4A to 5B, the contact lens 2 includes a contact lens body 20 and a glucose detection sheet 1 disposed on the contact lens body 20.

As shown in FIG. 1, the glucose detection sheet 1 includes a glucose recognition layer 11 including a photonic crystal array 112 formed in the glucose recognition layer 11, and the glucose recognition layer 11 is configured to recognize glucose.

In some embodiments, as shown in FIG. 1, the glucose recognition layer 11 is a molecularly imprinted photonic crystal layer 12.

Figure 2:
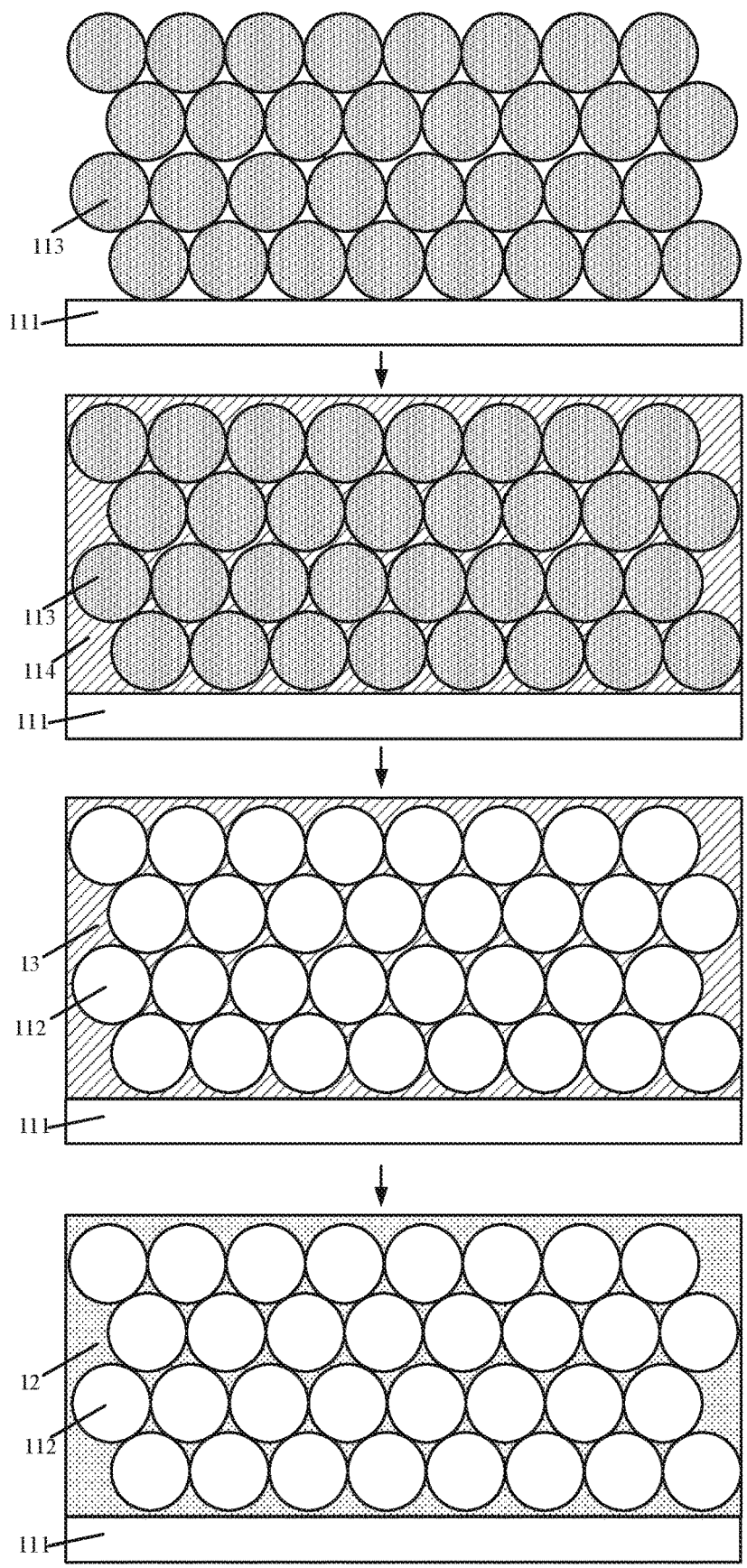
FIG. 2 is a schematic diagram showing a process of forming a molecularly imprinted photonic crystal layer, in accordance with some embodiments.

For example, as shown in FIG. 2, a method of forming the molecularly imprinted photonic crystal layer 12 may be as follows. A three-dimensional microsphere array 113 is formed on a base sheet 111 as a photonic crystal template; a glucose molecularly imprinted pre-polymerized solution 114 is added dropwise onto the base sheet 111, and is diffused into gaps of the three-dimensional microsphere array 113 by a siphon method; the glucose molecularly imprinted pre-polymerized solution 114 is thermally polymerized, so as to obtain a glucose molecularly imprinted polymer 13; the photonic crystal template is removed, so as to obtain the photonic crystal array 112; and imprinted template molecules (i.e. glucose molecules) of the glucose molecularly imprinted polymer 13 are removed, so as to obtain the molecularly imprinted photonic crystal layer 12. After the imprinted template molecules are removed, molecular recognition sites that are complementary to the imprinted template molecules in the space structure and function group are formed in the polymer backbone structure. In addition, after the molecularly imprinted photonic crystal layer 12 is formed, the base sheet 11 may be removed.

In some examples, the glucose molecularly imprinted pre-polymerized solution 114 includes glucose, at least one functional monomer, a recognition group, a cross-linking agent, an initiator, etc. For example, the at least one functional monomer includes hydroxyethyl methacrylate and N-isopropylacrylamide, the recognition group is 4-vinylbenzeneboronic acid, the cross-linking agent is N,N'-methylenebisacrylamide, and the initiator is 2,2'-azobisisoheptonitrile (CAS: 4419-11-8).

For example, the three-dimensional microsphere array 113 is self-assembled onto the base sheet 111 by a vertical deposition method.

For example, the three-dimensional microsphere array 113 is a polymethyl methacrylate microsphere array. In this way, sizes and shapes of gaps formed among adjacent several microspheres are substantially the same, and when the glucose molecularly imprinted pre-polymerized solution 114 is diffused into the gaps of the polymethyl methacrylate microsphere array by the siphon method, the glucose molecularly imprinted pre-polymerized solution 114 may be dispersed more evenly in the polymethyl methacrylate microsphere array. Therefore, the molecularly imprinted photonic crystal layer 12 may uniformly sense the glucose concentration in the user's tears, and the accuracy of detecting the glucose concentration in the user's tears may be further improved.

Herein, when a user wears the contact lens 2 described above, the glucose detection sheet 1 on the contact lens body 20 may sense the glucose concentration in the user's body by making contact with the user's tears. After the molecularly imprinted photonic crystal layer 12 of the glucose detection sheet 1 absorbs glucose in the user's tears, a spectrum redshift may occur in the molecularly imprinted photonic crystal layer 12 (that is, spectral lines move a certain distance towards a red end of the spectrum, indicating longer wavelengths and decreased frequencies). The spectral redshift is directly manifested as a change in a color of the glucose detection sheet 1 on the contact lens body 20. In this way, by observing a degree to which the color of the glucose detection sheet 1 changes, it may be possible to realize detection of a spectral redshift value of the glucose detection sheet 1, so as to determine the glucose concentration in the user's tears. Then, the glucose concentration in the user's blood may be calculated according to the glucose concentration in the user's tears, thereby realizing quick, non-invasive and inexpensive detection of the glucose concentration in the user's body.

It will be noted that the glucose concentration in human tears increases as the glucose concentration in the human blood increases, and decreases as the glucose concentration in the human blood decreases. It may be considered that a ratio of the glucose concentration in the human tears to the glucose concentration in the human blood is a fixed value, which is hereinafter referred to as a ratio coefficient X. For example, the glucose concentration in the human tears is one-fiftieth of the glucose concentration in the human blood. That is, the ratio coefficient X is 1/50.

On this basis, the method for calculating the glucose concentration in the user's blood based on the glucose concentration in the user's tears may be, for example, as follows: the glucose concentration in the user's blood is calculated according to the ratio coefficient X of the glucose concentration in the human tears to the glucose concentration in the human blood and the detected glucose concentration in the user's tears.

Figure 3A:
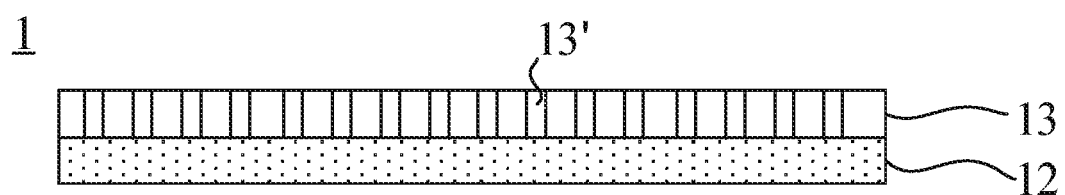
FIG. 3A is a schematic sectional view of a glucose detection sheet, in accordance with some embodiments.

In some embodiments, as shown in FIG. 3A, the glucose detection sheet 1 further includes a first substrate 13 disposed on a surface of the molecularly imprinted photonic crystal layer 12 facing away from the contact lens body 20. The first substrate 13 includes first pore structures 13' extending from a surface of the first substrate 13 facing the molecularly imprinted photonic crystal layer 12 to the opposite surface of the first substrate 13.

In some embodiments, since the first substrate 13 needs to make contact with the user's tears, a material of the first substrate 13 may be selected from materials having good breathability, skin affinity, and biocompatibility. For example, the first substrate 13 includes a paper-based substrate or a polymethyl methacrylate substrate. A flexible and thin paper material, such as filter paper or nano paper, may be used as the paper-based substrate.

The first pore structures 13' in the first substrate 13 connect the molecularly imprinted photonic crystal layer 12 to an outside of the glucose detection sheet 1. Therefore, it may be possible to use the first pore structures 13' in the first substrate 13 to increase an area of the molecularly imprinted photonic crystal layer 12 that is in contact with the user's tears. As a result, the molecularly imprinted photonic crystal layer 12 in the glucose detection sheet 1 may be more fully in contact with the user's tears, and the glucose detection sheet 1 may sense the glucose concentration more accurately, thereby improving an accuracy of detecting the glucose concentration in the user's tears.

Herein, a shape of the first pore structure 13' and a density of the first pore structures 13' are not specifically limited, and may be set according to actual needs. For example, the shape of a section of the first pore structure 13' may be round, square, irregular, strip-shaped, or the like. In a case where the section of first pore structure 13' is strip-shaped, the strip-shaped pore may have a tendency to extend from an inside to the outside of the first substrate 13, so as to connect the molecularly imprinted photonic crystal layer 12 to the outside of the glucose detection sheet 1. For example, the first pore structures 13' may be evenly distributed, so that any region of the molecularly imprinted photonic crystal layer 12 is fully in contact with the user's tears. Therefore, a portion of the molecularly imprinted photonic crystal layer 12 located in any region may absorb the glucose at substantially uniform.

Figure 3B:
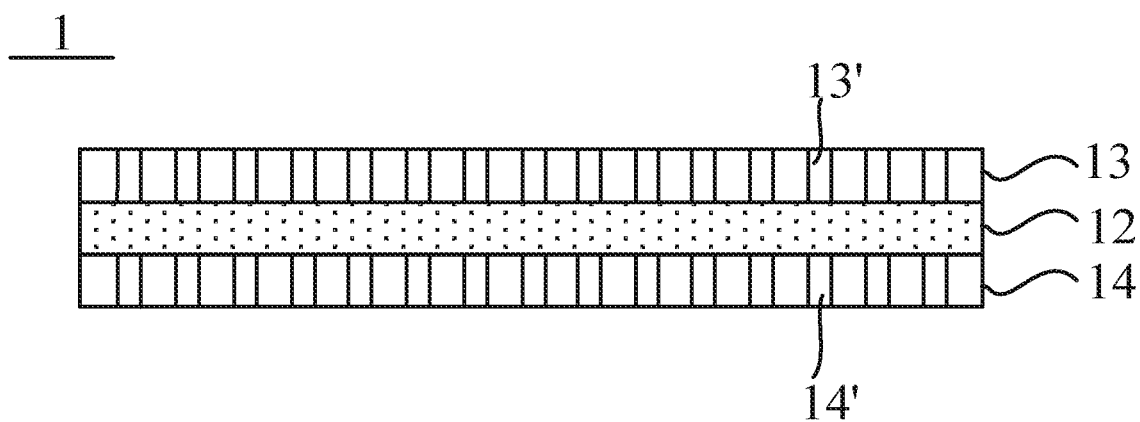
FIG. 3B is a schematic sectional view of another glucose detection sheet, in accordance with some embodiments.

In some other embodiments, as shown in FIG. 3B, in addition to the first substrate 13, the glucose detection sheet 1 further includes a second substrate 14. The second substrate 14 is disposed between and in contact with the molecularly imprinted photonic crystal layer 12 and the contact lens body 20. The second substrate 14 has second pore structures 14' extending from a surface of the second substrate 14 facing the molecularly imprinted photonic crystal layer 12 to its opposite surface.

Herein, with regard to the second pore structures 14', reference may be made to the first pore structures 13', and details are not described herein again.

In some embodiments, a material of the first substrate 13 and a material of the second substrate 14 are the same. In this way, the process of forming the glucose detection sheet 1 may be simplified.

Figure 4A:
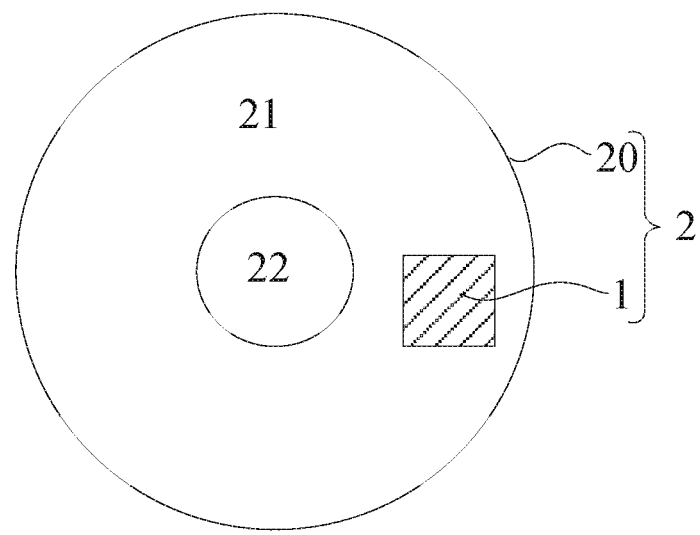
FIG. 4A is a schematic front view of a contact lens, in accordance with some embodiments.
Figure 4B:
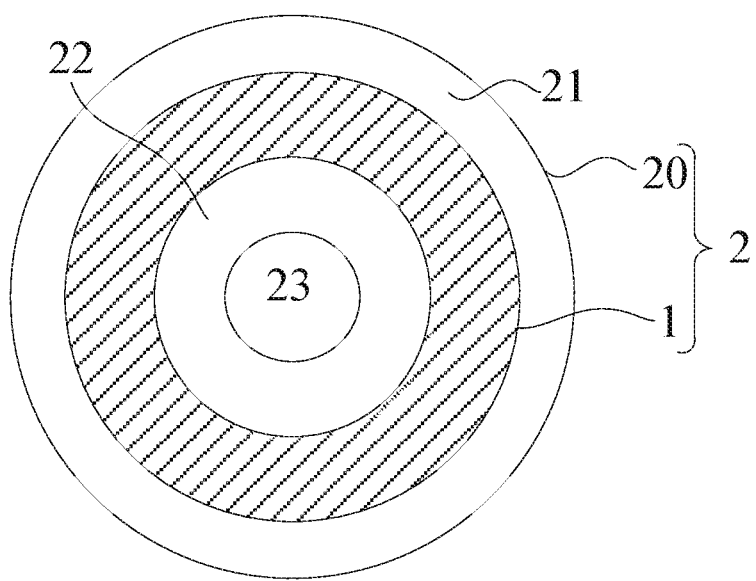
FIG. 4B is a schematic front view of another contact lens, in accordance with some embodiments.

In some embodiments, as shown in FIGS. 4A and 4B, the contact lens body 20 includes a corneal region 22 and an eye white region 21 around the corneal region 22, and the glucose detection sheet 1 is disposed on the eye white region 21 of the contact lens body 20. The eye white region 21 is a region of the contact lens body 20 that is used for contacting an eye white of the user' eyeball, and the corneal region 22 is a region of the contact lens body 20 that is used for contacting cornea of the user' eyeball.

In the manufacture of the contact lens 2, a glucose detection sheet 1 may be formed in the region of the contact lens body 20 that is used for contacting the eye white of the user' eyeball (for example, the glucose detection sheet 1 is attached onto the contact lens body 20). Then, a curved surface in the corneal region 22 of the contact lens body 20 corresponding to degree of the contact lens 20 is formed, so as to form the contact lens 2.

In some embodiments, after the contact lens 2 is worn for a period of time or after the contact lens 2 finishes detecting the glucose concentration in the user's body, the molecularly imprinted photonic crystal layer 12 in the glucose detection sheet 1 of the contact lens 2 has already absorbed glucose molecules in the user's tears. Then, after the contact lens 2 is taken out, the contact lens 2 may be immersed in a reducing immersion liquid, so as to dilute and dissolve the glucose molecules bound to the molecularly imprinted photonic crystal layer 12 in the contact lens 2 into the reducing immersion liquid, thereby facilitating a next wearing and detection.

Since the glucose detection sheet 1 uses the contact lens body 20 as a carrier, no matter on which surface of the contact lens body 20 the glucose detection sheet 1 is provided, the glucose detection sheet 1 is in contact with the user's tears to detect the glucose concentration in the user's tears.

Figure 5A:
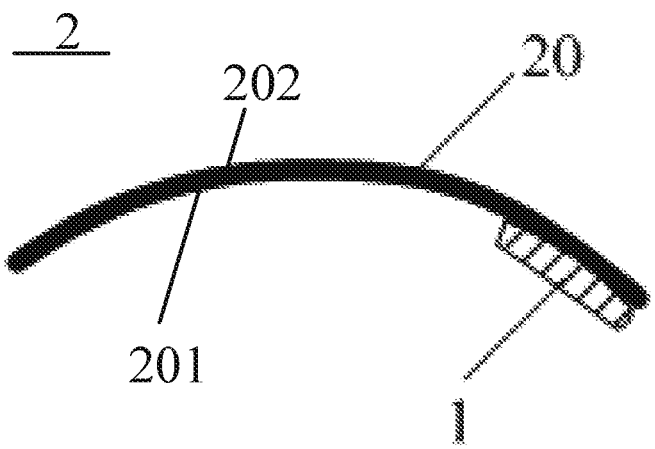
FIG. 5A is a schematic side view of a contact lens, in accordance with some embodiments.
Figure 5B:
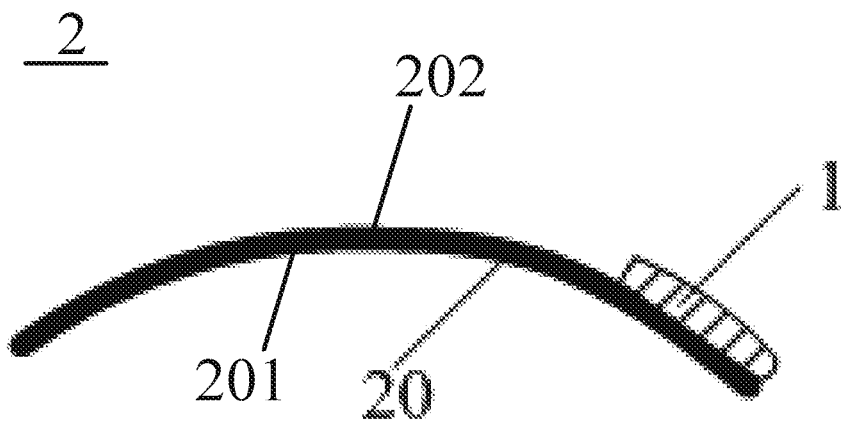
FIG. 5B is a schematic side view of another contact lens, in accordance with some embodiments.

In some embodiments, as shown in FIGS. 5A and 5B, the contact lens body 20 includes an eyeball contact surface 201 and a first surface 202 opposite to the eyeball contact surface 201. For example, as shown in FIG. 5A, the glucose detection sheet 1 is provided on the eyeball contact surface 201 of the contact lens body 20. That is, the glucose detection sheet 1 on the contact lens body 20 comes into contact with the user's eyeball when the user wears the contact lens 2. For another example, as shown in FIG. 5B, the glucose detection sheet 1 is provided on the first surface 202 of the contact lens body 20. That is, the glucose detection sheet 1 on the contact lens body 20 does not come into contact with the user's eyeball when the user wears the contact lens 2.

In some embodiments, the contact lens body 20 may be a polymethyl methacrylate substrate or a paper-based substrate. Herein, a flexible thin paper material, such as nano paper, may be used as the paper-based substrate.

In some embodiments, the contact lens body 20 and the second substrate 14 are made of a same material. In this case, the contact lens body 20 and the second substrate 14 may be integrally formed. For example, the material of the contact lens body 20 and the material of the second substrate 14 of the glucose detection sheet 1 are nano paper. In this way, the glucose detection sheet 1 may be directly formed with the contact lens body 20 as the substrate. Therefore, it may be possible to simplify a manufacturing process of the contact lens 2 and save manufacturing materials.

In some embodiments, a shape of the glucose detection sheet 1 may be set, according to actual needs, to be, for example, circular, square, rectangular as shown in FIG. 4A, or annular as shown in FIG. 4B, as long as a pupil of the user's eyeball is not blocked.

For example, as shown in FIG. 4B, the contact lens body 20 includes the corneal region 22 and the eye white region 21 around the corneal region 22, and the corneal region 22 includes a pupil region 23. As shown in FIG. 4B, the shape of the glucose detection sheet 1 is annular, and the annular glucose detection sheet 1 surrounds the pupil region 23 of the contact lens body 20. The pupil region 23 is a region of the contact lens body 20 that is used for contacting the pupil of the user' eyeball. In this way, it may be possible to effectively increase a contact area of the glucose detection sheet 1 and the user's tears without affecting a normal use of the contact lens 2, thereby improving an accuracy and efficiency of the glucose detection sheet 1 in detecting the glucose concentration in the user's body.

Figure 6:
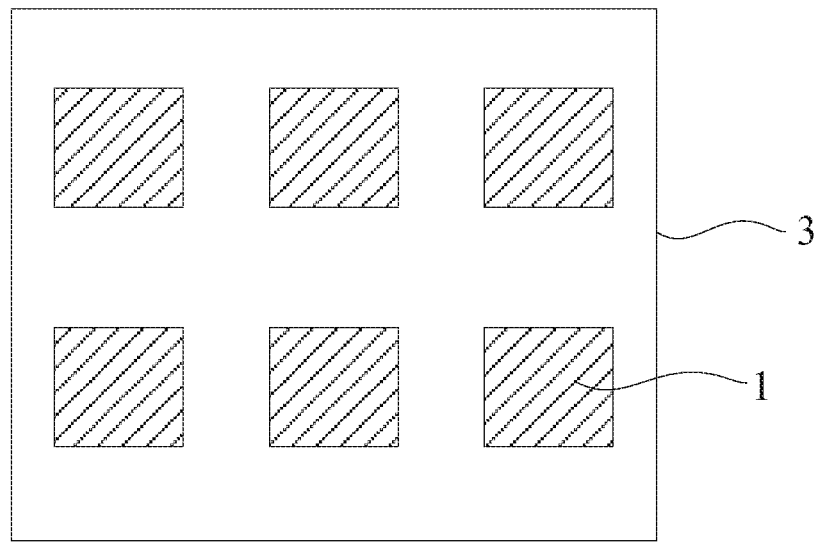
FIG. 6 is a schematic diagram of a glucose detection sensor, in accordance with some embodiments.

In some embodiments of the present disclosure, as shown in FIG. 6, a glucose detection sensor 3 is provided, including at least one glucose detection sheet 1 as described in some of the foregoing embodiments. The glucose detection sensor 3 may not only detect the glucose concentration in the user's body by contacting the user's tears, but may also detect the glucose concentration in the user's body by contacting other body fluids of the user, such as saliva or urine. In this way, a detection range of the glucose detection sensor 3 may be expanded.

In some embodiments, the at least one glucose detection sheet 1 includes a plurality of glucose detection sheets 1, and the plurality of glucose detection sheets 1 are arranged in an array (as shown in FIG. 6). In this way, the glucose detection sensor 3 may detect the glucose concentration in the user's body fluids comprehensively, so that a detection result may be more accurate.

Figure 7:
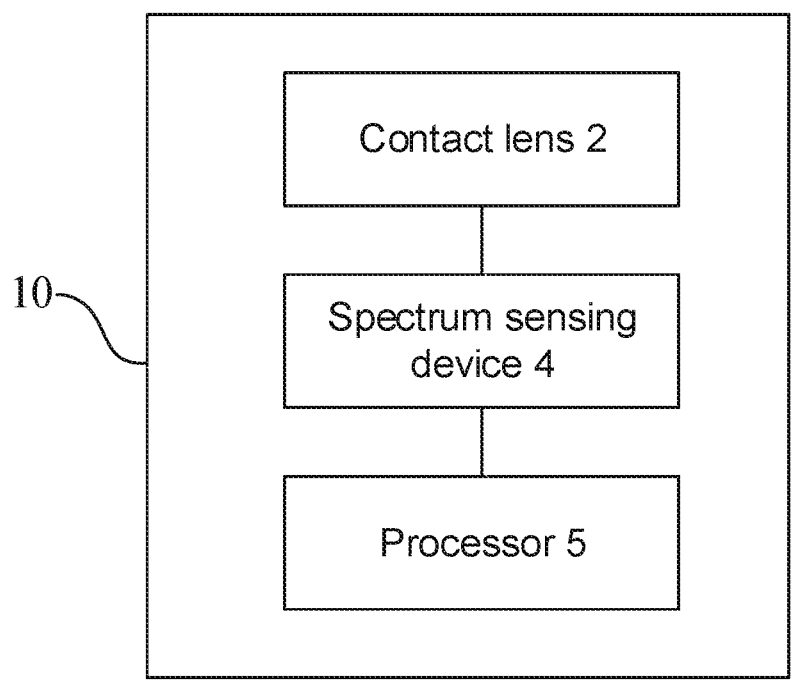
FIG. 7 is a schematic block diagram of a system for monitoring glucose, in accordance with some embodiments.

In some embodiments of the present disclosure, a system for monitoring glucose 10 is provided, which, as shown in FIG. 7, includes the contact lens 2 as described in any one of the foregoing embodiments, a spectrum sensing device 4, and a processor 5 coupled to the spectrum sensing device 4.

The spectrum sensing device 4 is configured to send a signal carrying spectral information of the glucose detection sheet 1 in the contact lens 2 to the processor 5 after the glucose detection sheet 1 senses the glucose concentration in the tears of the user.

The processor 5 is configured to obtain a spectral redshift value of the glucose detection sheet 1 in the contact lens 2 according to the signal, so as to determine the glucose concentration in the tears of the user. For example, the system for monitoring glucose 10 further includes a memory coupled to the processor 5, and the memory is configured to store a correspondence between the spectral redshift value and the glucose concentration value. In this case, the processor 5 determines the glucose concentration in the tears of the user according to the correspondence and the obtained spectral redshift value of the glucose detection sheet 1. The processor 5 may be a processor with spectral analysis function or a professional spectral analysis instrument.

Figure 8:
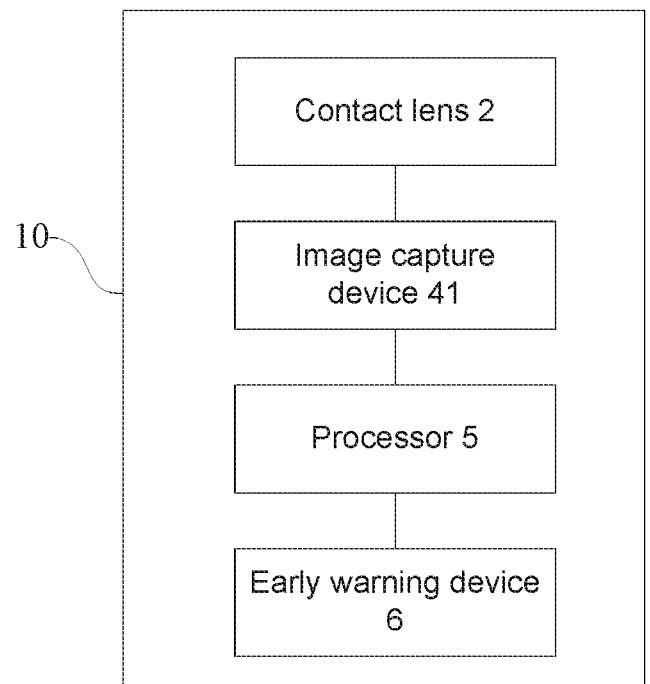
FIG. 8 is a schematic block diagram of another system for monitoring glucose, in accordance with some embodiments.

In some embodiments, as shown in FIG. 8, the spectrum sensing device 4 includes an image capture device 41 coupled to the processor 5. The image capture device 41 is configured to capture an image of the contact lens 2 after the glucose detection sheet 1 in the contact lens 2 senses the glucose concentration in the tears of the user, and send the image of the contact lens 2 to the processor 5. The image capture device 41 is placed, for example, opposite to the contact lens 2, so as to capture an image of the contact lens 2. The image capture device 41 may be a camera component, and the camera component is capable of capturing images with high definition, so that it is possible to obtain a clearer image of the contact lens 2 after the glucose detection sheet 1 in the contact lens 2 senses the glucose concentration in an object to be detected. For example, the camera component is a web camera, a camera, etc.

The processor 5 is configured to perform spectral analysis on the image of the contact lens 2 (the image includes spectral information of the glucose detection sheet 1 in the contact lens 2) captured by the image capture device 41 after receiving the image, so as to obtain a spectrum. Then, the processor 5 is configured to: compare the spectrum with a spectrum of an image of the glucose detection sheet 1 obtained before it senses the glucose concentration in the tears, to obtain a spectral redshift value of the glucose detection sheet 1 after it senses the glucose concentration in the user's tears; and obtain a glucose concentration in the object to be detected according to the spectral redshift value.

In some embodiments, as shown in FIG. 8, the system for monitoring glucose 10 further includes an early warning device 6 coupled to the processor 5. The processor 5 is further configured to determine whether the glucose concentration in the tears of the user is within a preset threshold range, and send a warning control signal to the early warning device 6 in response to a determination that the glucose concentration in the tears of the user is not within the preset threshold range.

On this basis, the early warning device 6 is configured to send out a warning signal in response to receiving the warning control signal. For example, the description that the glucose concentration in the tears of the user is not within the preset threshold range includes the following situations: the glucose concentration in the tears of the user is less than a lower limit of the preset threshold range, or the glucose concentration in the tears of the user is greater than an upper limit of the preset threshold range. For example, the early warning device 6 is an electronic alarm, which sends out a warning signal in the form of sound, light, vibration, or the like.

In this way, the glucose concentration in the user's tears may be determined by detecting a degree to which the glucose detection sheet 1 is red-shifted after it senses the glucose concentration in the user's tears. If the processor 5 determines that the glucose concentration in the user's tears is not within the preset threshold range, the early warning device 6 sends out a warning signal. With this solution, not only the glucose concentration in the user's body may be detected in a quick, non-invasive and inexpensive way, but also the user may be alerted when the glucose concentration in the tears is not within the preset threshold range.

Herein, the preset threshold range may be set according to a preset glucose concentration range in the human blood. For example, if the preset glucose concentration range in the human blood is: L min≤L≤L max (L is a glucose concentration in the human blood, L min is a lower limit of the preset glucose concentration range in the human blood, and L max is an upper limit of the preset glucose concentration range in the human blood), and a ratio coefficient of the glucose concentration in the human tears to the glucose concentration in the human blood is X, then the preset threshold range is: a production of L min and X≤P≤a product of L max and X (P is the glucose concentration in the human tears).

For example, for a normal person (a person without hyperglycemia, hypoglycemia, or diabetes may be considered a normal person), the preset glucose concentration range in the human blood may be a normal glucose concentration range in the blood of the human without hyperglycemia, hypoglycemia, or diabetes, and the preset threshold range may be set according to the normal glucose concentration range in the human blood.

On this basis, for example, a lower limit of the glucose concentration in the blood of a normal person is 4 mmol/L (80 mg/dL), and an upper limit of the glucose concentration is 7 mmol/L (120 mg/dL). That is, the normal glucose concentration range in the human blood is: 4 mmol/L≤L≤7 mmol/L (or 80 mg/dL≤L≤120 mg/dL). In a case where the object to be detected is the user's tears, if the ratio coefficient X of the glucose concentration in the human tears to the glucose concentration in the human blood is 1/50, then the lower limit of the glucose concentration in the human tears corresponding to the lower limit of the glucose concentration in the human blood is 0.08 mmol/L (1.6 mg/dL), and the upper limit of the glucose concentration in the human tears corresponding to the upper limit of the glucose concentration in the human blood is 0.14 mmol/L (2.4 mg/dL). That is, the preset threshold range may be set to: 0.08 mmol/L≤P≤0.14 mmol/L (or 1.6 mg/dL≤P≤2.4 mg/dL).

In the above case, when the glucose concentration in the user's tears is not within the preset threshold range, the early warning device 6 will send out a warning signal to remind the user to pay attention to the glucose concentration in his/her body. In this case, the user can control the glucose concentration in his/her body through diet or other non-medicine adjustment methods.

For another example, for patients with hypoglycemia or diabetes, the lower limit and upper limit of the preset glucose concentration range in the human blood may be glucose concentrations of patients with hypoglycemia or diabetes that need to be adjusted. Then, the preset threshold range may be set according to the preset glucose concentration range in the human blood.

In the above case, when the glucose concentration in the user's tears is not within the preset threshold range, the early warning device 6 will send out a warning signal to remind patients with hypoglycemia to ingest foods or medicines containing glucose to increase the glucose concentration in the body, or to remind patients with diabetes to inject insulin to reduce the glucose concentration in the body.

Figure 9:
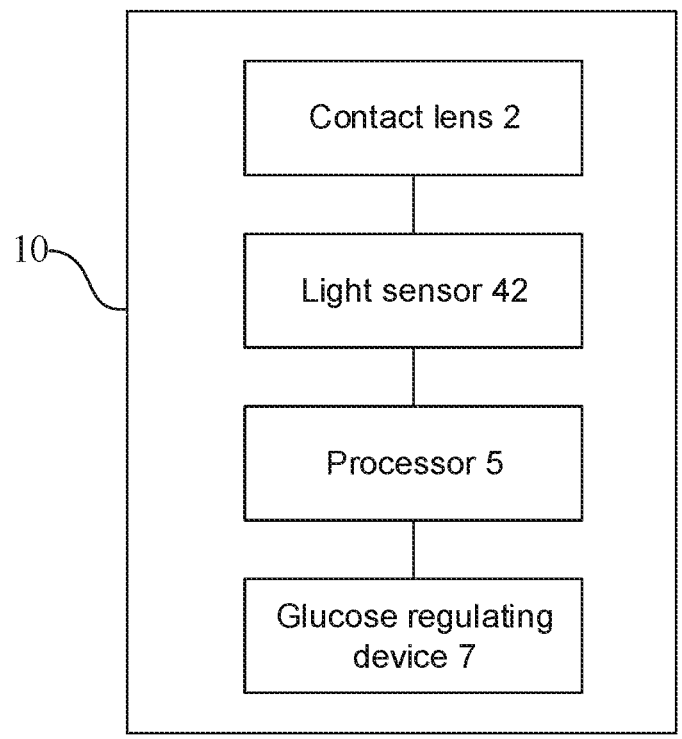
FIG. 9 is a schematic block diagram of yet another system for monitoring glucose, in accordance with some embodiments.
Figure 10A:
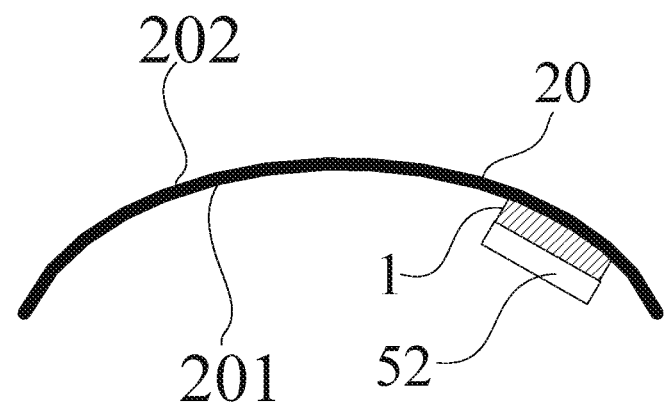
FIG. 10A is a schematic side view of a structure including both a light sensor and a contact lens, in accordance with some embodiments.
Figure 10B:
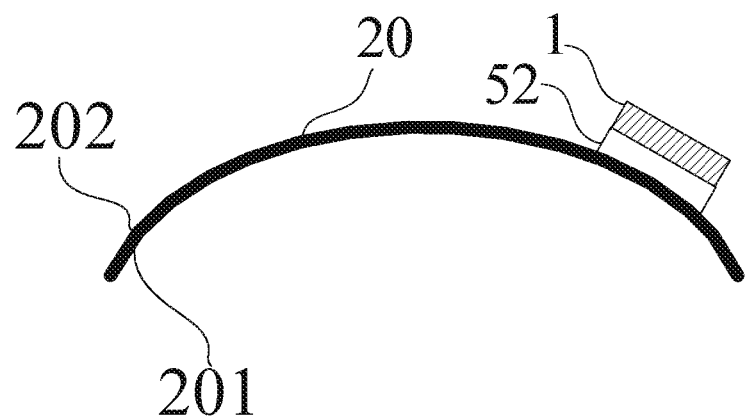
FIG. 10B is a schematic side view of another structure including both a light sensor and a contact lens, in accordance with some embodiments.

In some other embodiments, as shown in FIG. 9, the spectrum sensing device 4 includes a light sensor 42 coupled to the processor 5. The light sensor 42 is provided on the glucose detection sheet 1, and a sensing surface of the light sensor 42 faces the glucose detection sheet 1. For example, as shown in FIG. 10A, in a case where the glucose detection sheet 1 is disposed on the eyeball contact surface 201 of the contact lens body 20, the light sensor 42 is disposed on a surface of the glucose detection sheet 1 facing away from the contact lens body 20. Or, as shown in FIG. 10B, in a case where the glucose detection sheet 1 is disposed on the first surface 202 of the contact lens body 20, the light sensor 42 is provided on a surface of the glucose detection sheet 1 proximate to the contact lens body 20, that is, the light sensor 42 is disposed between the glucose detection sheet 1 and the contact lens body 20.

The light sensor 42 is configured to sense light with wavelengths in a range of spectrum of the glucose detection sheet 1 after the glucose detection sheet 1 senses the glucose concentration in the tears of the user, generate a sensing signal carrying spectral information, and send the generated sensing signal to the processor 5. The processor 5 is configured to: obtain the spectrum of the glucose detection sheet 1 after the glucose detection sheet 1 senses the glucose concentration in the tears of the user according to the sensing signal; compare the spectrum with a spectrum of an image of the glucose detection sheet 1 obtained before it senses the glucose concentration in the tears to obtain a spectral redshift value of the glucose detection sheet 1 after it senses the glucose concentration in the user's tears; and obtain a glucose concentration in the object to be detected according to the spectral redshift value.

Herein, the light sensor 42 is matched with the glucose detection sheet 1 in the contact lens 2, and is configured to sense the light with wavelengths in the range of spectrum of the glucose detection sheet 1 in real time. The light sensor 42 may be a photodiode. For example, the sensing signal may be an electric signal or other signals carrying spectral information. In this case, the processor 5 is configured to obtain the spectral redshift value of the glucose detection sheet 1 according to the sensing signal. It will be noted that the light sensor 42 may be coupled to the processor 5 through wired or wireless manner.

In some embodiments, as shown in FIG. 9, the system for monitoring glucose 10 further includes a glucose regulating device 7 coupled to the processor 5. The processor 5 is further configured to determine whether the spectral redshift value of the glucose detection sheet 1 exceeds a redshift threshold, and send a regulating control signal to the glucose regulating device 7 in response to a determination that the spectral redshift value exceeds the redshift threshold.

The redshift threshold may be set according to the upper limit of the preset glucose concentration in the human blood. For example, the upper limit of the glucose concentration in the blood of a normal person is 7 mmol/L (120 mg/dL), and the spectral redshift value is a spectral redshift value that is obtained when the glucose detection sheet 1 senses the glucose concentration of 7 mmol/L. The redshift threshold may also be set according to actual testing results.

The glucose regulating device 7 is configured to release a substance for reducing glucose concentration in response to receiving the regulating control signal.

In this way, the system for monitoring glucose 10 provided in the foregoing embodiments may use the contact lens 2 to sense the glucose concentration in the human body in real time in a non-invasive and inexpensive way.

In some embodiments, the glucose regulating device 7 includes an insulin releasing device capable of being implanted under skin of the user. In this way, the insulin releasing device releases insulin into the user's body in response to the regulating control signal.

Figure 11:
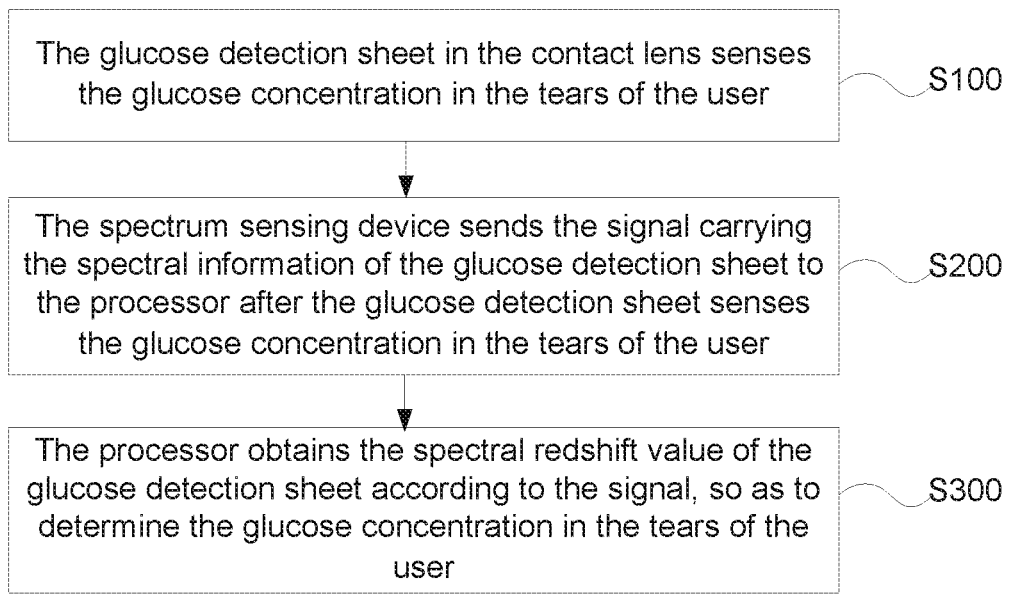
FIG. 11 is a schematic flowchart of a method for monitoring glucose, in accordance with some embodiments.

In some embodiments of the present disclosure, a method for monitoring glucose is provided. The method for monitoring glucose is performed by the system for monitoring glucose 10 described in the above embodiments. As shown in FIG. 11, the method for monitoring glucose includes step 100 to step 300 (S100 to S300).

In S100, the glucose detection sheet 1 in the contact lens 2 senses the glucose concentration in the tears of the user.

In the above step, the glucose detection sheet 1 in the contact lens 2 will make contact with the user's tears. The spectrum red-shift may occur in the glucose recognition layer 11 including the photonic crystal array 112 in the glucose detection sheet 1 due to the existence of the glucose in the tears of the user. That is, a color of the glucose detection sheet 1 will change.

In S200, the spectrum sensing device 4 sends the signal carrying the spectral information of the glucose detection sheet 1 to the processor 5 after the glucose detection sheet 1 senses the glucose concentration in the tears of the user.

In S300, the processor 5 obtains the spectral redshift value of the glucose detection sheet 1 according to the signal, so as to determine the glucose concentration in the tears of the user.

Figure 12:
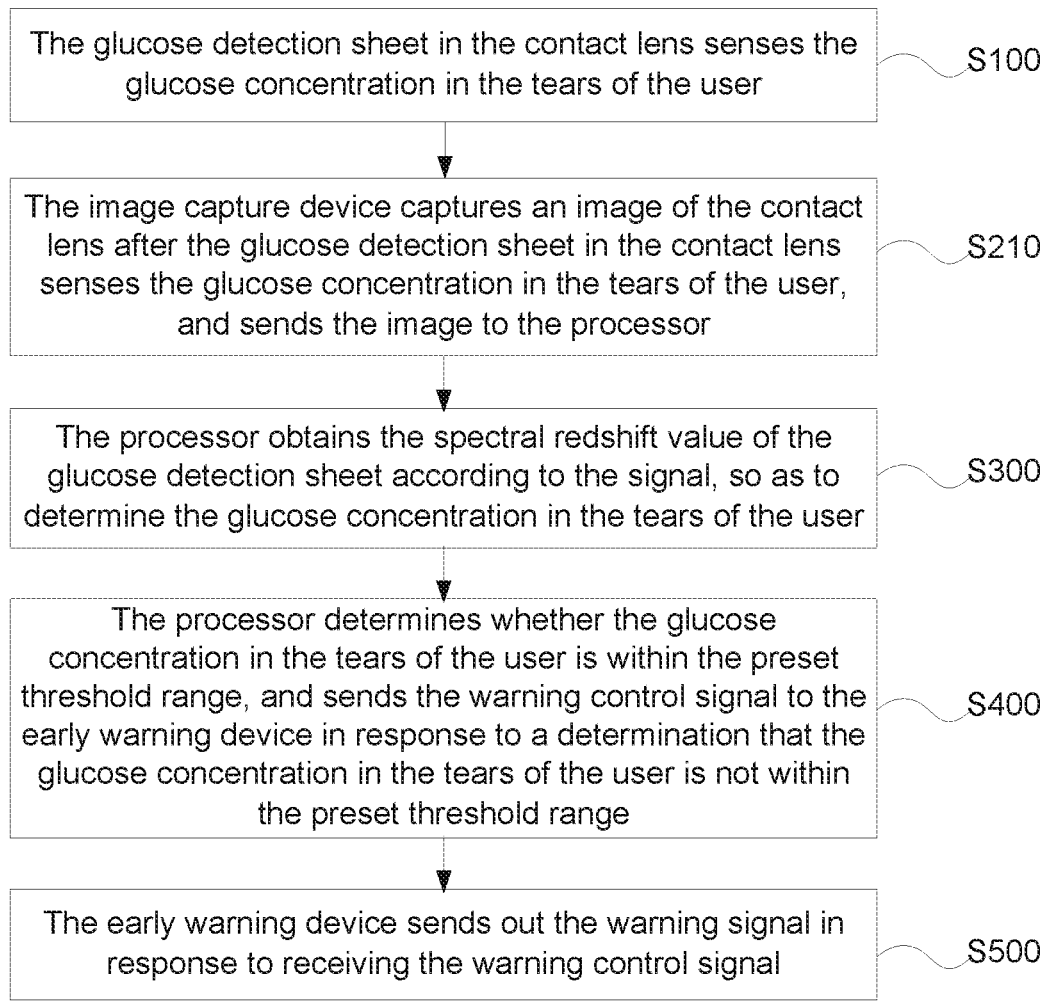
FIG. 12 is a schematic flowchart of another method for monitoring glucose, in accordance with some embodiments.

In some embodiments, the spectrum sensing device 4 includes an image capture device 41. Based on this, as shown in FIG. 12, S200 in the method for monitoring glucose includes step 210 (S210).

In S210, the image capture device 41 captures an image of the contact lens 2 after the glucose detection sheet 1 in the contact lens 2 senses the glucose concentration in the tears of the user, and sends the image to the processor 5.

In the above step, the image capture device 41 may be used to take a picture of the contact lens 2 and ensure that the contact lens 2 accurately falls into an image collection region of the image capture device 41. When the image capture device 41 is used to take a picture of the contact lens 2, the image capture device 41 may be adjusted to focus on the user's eye, so as to ensure that the contact lens 2 is clearly photographed.

In the above step, after the image capture device 41 sends the image of the contact lens 2 to the processor 5, the processor 5 will perform picture cropping, feature extraction, and other operations on the image, so as to accurately determine the spectral redshift value of the glucose detection sheet 1 and further determine the glucose concentration in the user's tears according to the spectral redshift value. For example, in a case where the image is displayed in a RGB (red, blue and green) color mode, the spectral redshift value is reflected in the R value in the image information.

In some embodiments, the system for monitoring glucose 10 further includes an early warning device 6 coupled to the processor 5. In this case, as shown in FIG. 12, the method for monitoring glucose further includes step 400 and step 500 (S400 and S500).

In S400, the processor 5 determines whether the glucose concentration in the tears of the user is within the preset threshold range, and sends the warning control signal to the early warning device 6 in response to a determination that the glucose concentration in the tears of the user is not within the preset threshold range.

In S500, the early warning device 6 sends out the warning signal in response to receiving the warning control signal.

In S400, the processor 5 determines that the current detection of the glucose concentration is finished in response to a determination that the glucose concentration in the user's tears is within the preset threshold range, and a next detection will be performed.

The glucose concentration in the object to be detected may be detected in real time. In this case, the above description that "a next detection will be performed" means that the next detection will be performed immediately after the current detection is finished. The glucose concentration in the object to be detected may also be detected periodically. In this case, the above description that "a next detection will be performed" means that after the current detection is finished, the next detection will not be performed until a next cycle begins. The glucose concentration in the object to be detected may also be detected non-periodically. In this case, the above description that "a next detection will be performed" means that after the current detection is finished, the next detection will not be performed until a next time point set by the system or until the user manually triggers the system according to actual needs.

In the method for monitoring glucose, the contact lens 2 is used to sense the glucose concentration in the user's body, and the image capture device 41 and the processor 5 are used to obtain an accurate spectral redshift value of the glucose detection sheet 1 in the contact lens 2. In this way, it may be possible to determine the glucose concentration in the user's tears, and use the early warning device 6 to give a certain health reminder or early warning.

Figure 13:
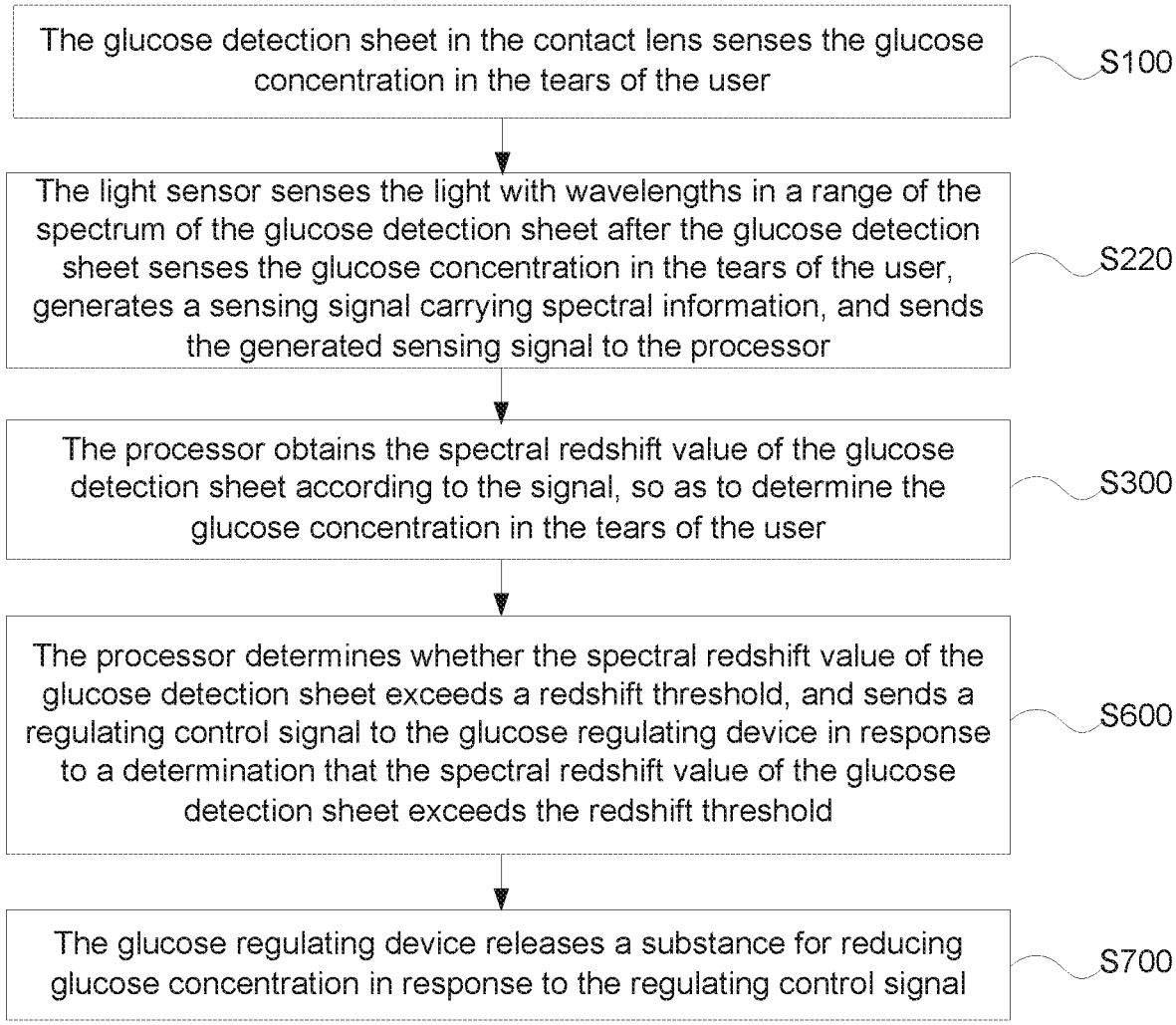
FIG. 13 is a schematic flowchart of yet another method for monitoring glucose, in accordance with some embodiments.

In some other embodiments, the spectrum sensing device 4 includes a light sensor 42. In this case, as shown in FIG. 13, S200 in the above monitoring method includes step 220 (S220).

In S220, the light sensor 42 senses the light with wavelengths in a range of the spectrum of the glucose detection sheet 1 after the glucose detection sheet 1 senses the glucose concentration in the tears of the user, generates a sensing signal carrying spectral information, and sends the generated sensing signal to the processor 5.

In some embodiments, the system for monitoring glucose 10 further includes a glucose regulating device 7 coupled to the processor 5. In this case, as shown in FIG. 13, the method for monitoring glucose further includes step 600 and step 700 (S600 and S700).

In S600, the processor 5 determines whether the spectral redshift value of the glucose detection sheet 1 exceeds a redshift threshold, and sends a regulating control signal to the glucose regulating device 7 in response to a determination that the spectral redshift value of the glucose detection sheet 1 exceeds the redshift threshold.

In S700, the glucose regulating device 7 releases a substance for reducing glucose concentration in response to the regulating control signal.

In S600, the processor 5 determines that the current detection of the glucose concentration is finished in response to a determination that the processor 5 determines that the spectral redshift value of the glucose detection sheet 1 does not exceed the redshift threshold, and the next detection will be performed.

In S220, S600, and S700, the light sensor 42 is used to sense light with wavelengths in a range of spectrum of the glucose detection sheet 1 in the contact lens 2 in real time, and generate the sensing signal carrying the spectral information. If the processor 5 determines that the spectral redshift value of the glucose detection sheet 1 exceeds the redshift threshold according to the spectral information, the processor 5 will send a regulating control signal to the glucose regulating device 7, so that the glucose regulating device 7 may regulate the glucose concentration in the user's body according to the regulating control signal.

In the method for monitoring glucose, the contact lens 2 is used to sense the glucose concentration in the human body in real time in a non-invasive and inexpensive way. In a case where the glucose concentration in the user's tears detected by the light sensor 42 is too high, the glucose regulating device 7 coupled to the processor 5 may regulate the glucose concentration in the user's body timely, automatically and effectively.

It will be noted that the glucose regulation disclosed in the embodiments of the present disclosure includes at least one of normal level regulation and disease level regulation. The normal level regulation is for the normal population, and the disease level regulation is for diabetic patients with high glucose concentrations or hypoglycemic patients with low glucose concentrations. A threshold of normal level regulation is lower than a threshold of disease level regulation.

In the description of the above embodiments, specific features, structures, materials or characteristics may be combined in any suitable manner in any one or more embodiments or examples.

The forgoing descriptions are merely specific implementation manners of the present disclosure, but the protection scope of the present disclosure is not limited thereto. Any person skilled in the art could readily conceive of changes or replacements within the technical scope of the present disclosure, which shall all be included in the protection scope of the present disclosure. Therefore, the protection scope of the present disclosure shall be subject to the protection scope of the claims.

What is claimed is:

1. A contact lens, comprising:
   a contact lens body; and
   a glucose detection sheet disposed on the contact lens body, wherein the glucose detection sheet includes:
     a glucose recognition layer including a photonic crystal array provided therein, and the glucose recognition layer being configured to recognize glucose.

2. The contact lens according to claim 1, wherein the glucose recognition layer is a molecularly imprinted photonic crystal layer.

3. The contact lens according to claim 2, wherein the glucose detection sheet further includes:
a first substrate disposed on a surface of the molecularly imprinted photonic crystal layer facing away from the contact lens body, the first substrate having first pore structures.

4. The contact lens according to claim 3, wherein the first substrate includes a paper-based substrate or a polymethyl methacrylate substrate.

5. The contact lens according to claim 3, wherein the glucose detection sheet further includes:
a second substrate disposed between and in contact with the molecularly imprinted photonic crystal layer and the contact lens body, the second substrate having second pore structures.

6. The contact lens according to claim 5, wherein a material of the first substrate and a material of the second substrate are the same.

7. The contact lens according to claim 5, wherein a material of the contact lens body and a material of the second substrate are the same, and the contact lens body and the substrate are integrally formed.

8. The contact lens according to claim 1, wherein the contact lens body includes an eyeball contact surface and a first surface opposite to the eyeball contact surface; and
the glucose detection sheet is disposed on the eyeball contact surface of the contact lens body or the first surface of the contact lens body.

9. The contact lens according to claim 1, wherein the contact lens body includes a corneal region and an eye white region around the corneal region, and the glucose detection sheet is disposed on the eye white region of the contact lens body.

10. The contact lens according to claim 1, wherein a shape of the glucose detection sheet is a rectangle, a circle, or a ring.

11. The contact lens according to claim 10, wherein the contact lens body includes a corneal region and an eye white region around the corneal region, and the corneal region includes a pupil region; and
the shape of the glucose detection sheet is a ring, and the glucose detection sheet surrounds the pupil region of the contact lens body.

12. A system for monitoring glucose, comprising:
the contact lens according to claim 1;
a spectrum sensing device configured to send a signal carrying spectral information of the glucose detection sheet in the contact lens to a processor after the glucose detection sheet senses a glucose concentration in tears of a user; and
the processor coupled to the spectrum sensing device and configured to obtain a spectral redshift value of the glucose detection sheet according to the signal, so as to determine the glucose concentration in the tears of the user.

13. The system for monitoring glucose according to claim 12, wherein the spectrum sensing device includes an image capture device configured to:
capture an image of the contact lens after the glucose detection sheet senses the glucose concentration in the tears of the user, and
send the image of the contact lens to the processor; and
the processor is configured to obtain a spectral redshift value of the glucose detection sheet according to the image of the contact lens.

14. The system for monitoring glucose according to claim 13, further comprising an early warning device coupled to the processor, wherein the processor is further configured to:
determine whether the glucose concentration in the tears of the user is within a preset threshold range, and
send a warning control signal to the early warning device in response to a determination that the glucose concentration in the tears of the user is not within the preset threshold range; and
the early warning device is configured to send out a warning signal in response to receiving the warning control signal.

15. The system for monitoring glucose according to claim 12, wherein the spectrum sensing device includes a light sensor;
the light sensor is disposed on the glucose detection sheet, and a sensing surface of the light sensor faces the glucose detection sheet; and
the light sensor is configured to:
sense light with wavelengths in a range of a spectrum of the glucose detection sheet after the glucose detection sheet senses the glucose concentration in the tears of the user,
generate a sensing signal carrying spectral information, and
send the sensing signal to the processor; and
the processor is configured to obtain the spectral redshift value of the glucose detection sheet according to the sensing signal.

16. The system for monitoring glucose according to claim 15, further comprising a glucose regulating device coupled to the processor, wherein the processor is further configured to determine whether the spectral redshift value of the glucose detection sheet exceeds a redshift threshold, and send a regulating control signal to the glucose regulating device in response to a determination that the spectral redshift value exceeds the redshift threshold; and
the glucose regulating device is configured to release a substance for reducing glucose concentration in response to receiving the regulating control signal.

17. The system for monitoring glucose according to claim 16, wherein the glucose regulating device includes an insulin releasing device capable of being implanted under skin of the user.

18. A method for monitoring glucose performed by the system for monitoring glucose according to claim 12, the method comprising:
sensing, by the glucose detection sheet in the contact lens, the glucose concentration in the tears of the user;
sending, by the spectrum sensing device, the signal carrying the spectral information of the glucose detection sheet to the processor after the glucose detection sheet senses the glucose concentration in the tears of the user;
obtaining, by the processor, the spectral redshift value of the glucose detection sheet according to the signal, so as to determine the glucose concentration in the tears of the user.

19. The method according to claim 18, wherein the system for monitoring glucose further includes an early warning device, and the method further comprises:
determining, by the processor, whether the glucose concentration in the tears of the user is within a preset threshold range;

sending, by the processor, the warning control signal to the early warning device in response to a determination that the glucose concentration in the tears of the user is not within the preset threshold range; and sending out, by the early warning device, an warning signal in response to the warning control signal.

20. The method according to claim 18, wherein the system for monitoring glucose further includes a glucose regulating device, and the method further comprises:

determining, by the processor, whether the spectral redshift value of the glucose detection sheet exceeds a redshift threshold;

sending, by the processor, a regulating control signal to the glucose regulating device in response to a determination that the spectral redshift value of the glucose detection sheet exceeds the redshift threshold; and releasing, by the glucose regulating device, a substance for reducing glucose concentration in response to the regulating control signal.

\* \* \* \* \*